(12) United States Patent
Samuel et al.

(10) Patent No.: US 7,824,435 B2
(45) Date of Patent: Nov. 2, 2010

(54) THERAPEUTIC LIGHT-EMITTING DEVICE

(75) Inventors: Ifor David William Samuel, St Andrews (GB); James Ferguson, Fife (GB)

(73) Assignee: The University Court of the University of St. Andrews and Tayside Health Board (GB)

( * ) Notice: Subject to any disclaimer, the term of this patent is extended or adjusted under 35 U.S.C. 154(b) by 874 days.

(21) Appl. No.: 10/494,695

(22) PCT Filed: Nov. 15, 2002

(86) PCT No.: PCT/GB02/05145

§ 371 (c)(1),
(2), (4) Date: Oct. 28, 2004

(87) PCT Pub. No.: WO03/043697

PCT Pub. Date: May 30, 2003

(65) Prior Publication Data

US 2005/0070976 A1    Mar. 31, 2005

(30) Foreign Application Priority Data

Nov. 17, 2001    (GB)    ................................. 0127581.7

(51) Int. Cl.
*A61N 5/06*    (2006.01)

(52) U.S. Cl. .......................................... 607/88; 607/90
(58) Field of Classification Search ............. 607/88–94; 606/9, 10
See application file for complete search history.

(56) References Cited

U.S. PATENT DOCUMENTS

| | | | | |
|---|---|---|---|---|
| 5,703,436 A | * | 12/1997 | Forrest et al. | ................ 313/506 |
| 5,827,186 A | * | 10/1998 | Chen et al. | ................... 600/407 |
| 5,944,748 A | * | 8/1999 | Mager et al. | ................... 607/88 |
| 6,096,066 A | * | 8/2000 | Chen et al. | ..................... 607/88 |
| 6,676,655 B2 | * | 1/2004 | McDaniel | ....................... 606/9 |
| 6,764,501 B2 | * | 7/2004 | Ganz | ............................ 607/92 |
| 6,936,044 B2 | * | 8/2005 | McDaniel | ....................... 606/9 |
| 2001/0000005 A1 | * | 3/2001 | Forrest et al. | ........... 204/192.12 |

* cited by examiner

*Primary Examiner*—Ahmed M Farah
(74) *Attorney, Agent, or Firm*—Barnes & Thornburg LLP

(57) ABSTRACT

An ambulatory device for use in a therapeutic and/or cosmetic treatment, the device comprises an organic light-emitting semiconductor which, in use, covers an area to be treated and emits electromagnetic radiation to cause said therapeutic and/or cosmetic treatment of the area. The light source may be extensive to provide uniform irradiation of the area to be treated and may be pulsed. The device may also include a photopharmaceutical.

12 Claims, 10 Drawing Sheets

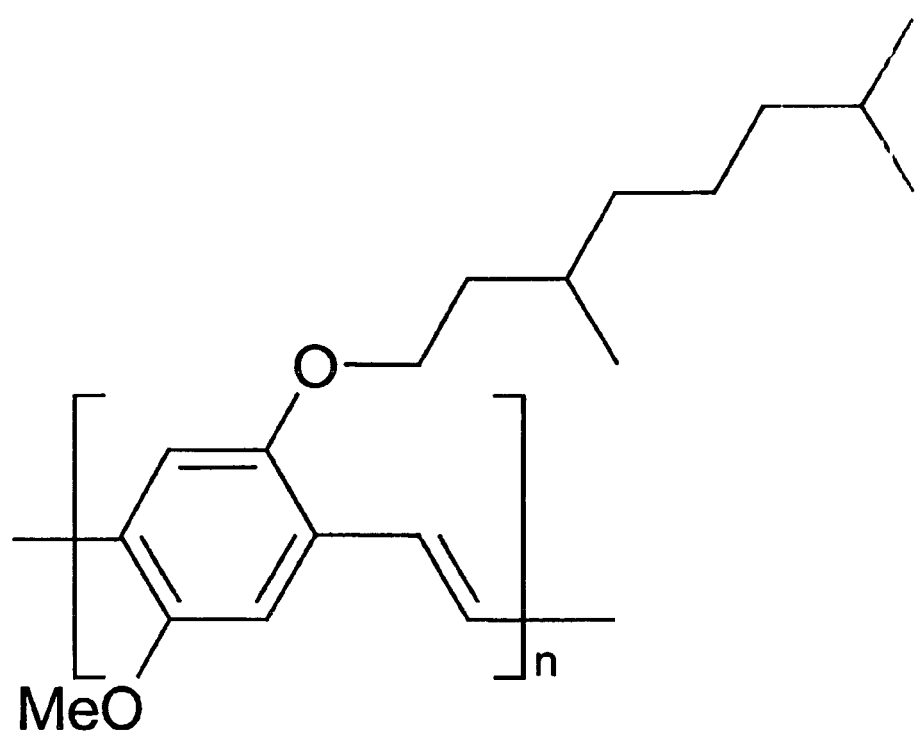
Figure 2: Chemical structure of the polymer $OC_1C_{10}$-PPV

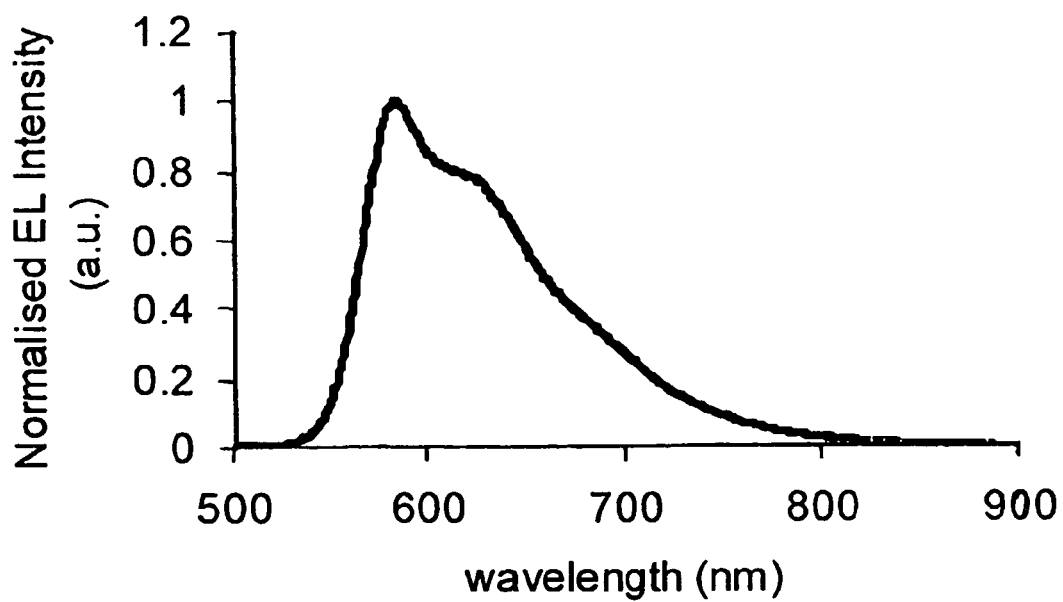
Figure 3: Spectrum of light emitted by device using $OC_1C_{10}$-PPV as the light-emitting layer

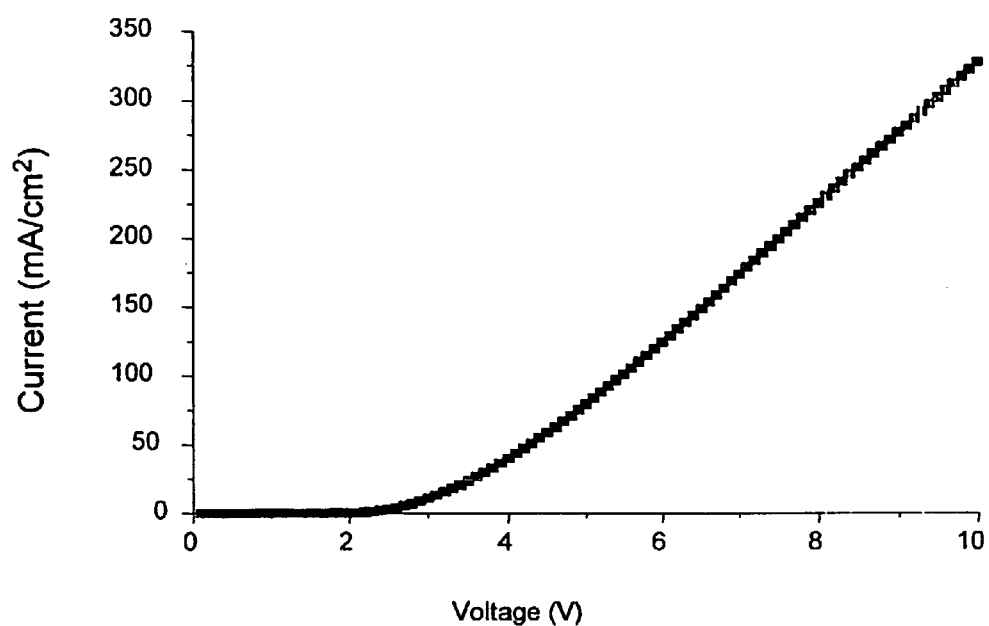
Figure 4(a): Current-voltage characteristics of device in figure 3

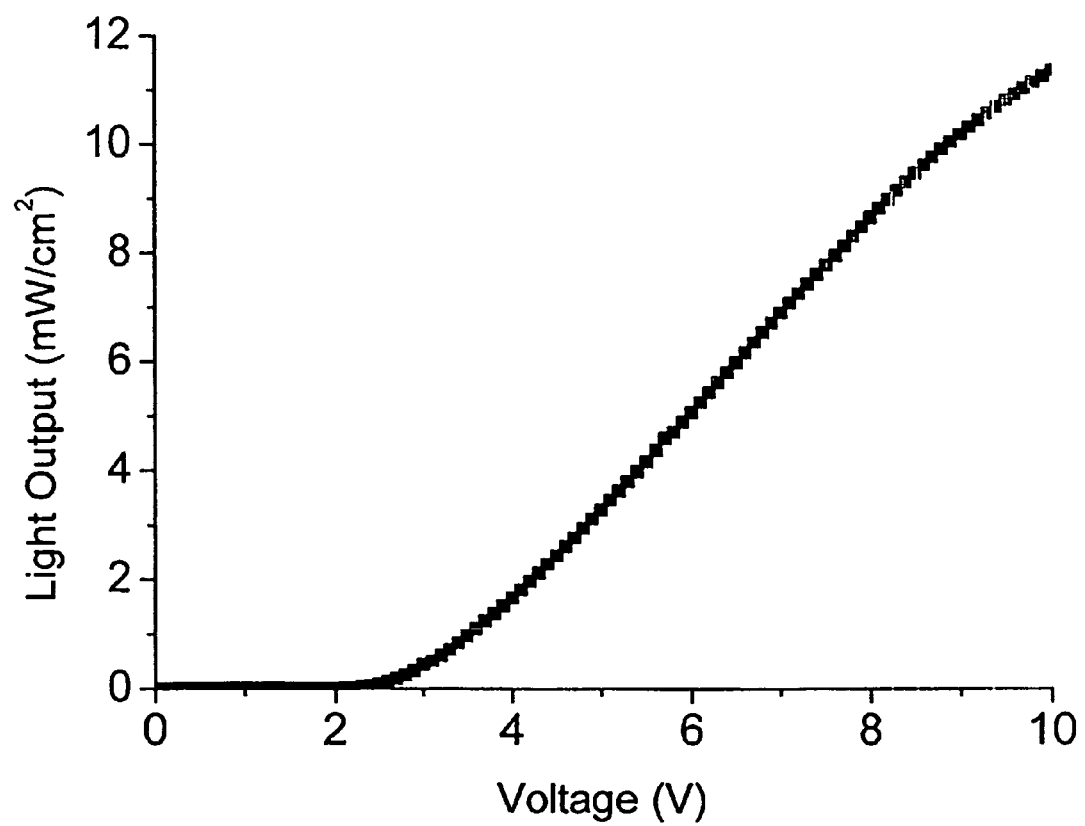
Figure 4(b): Light output-voltage characteristics of device in figure 3

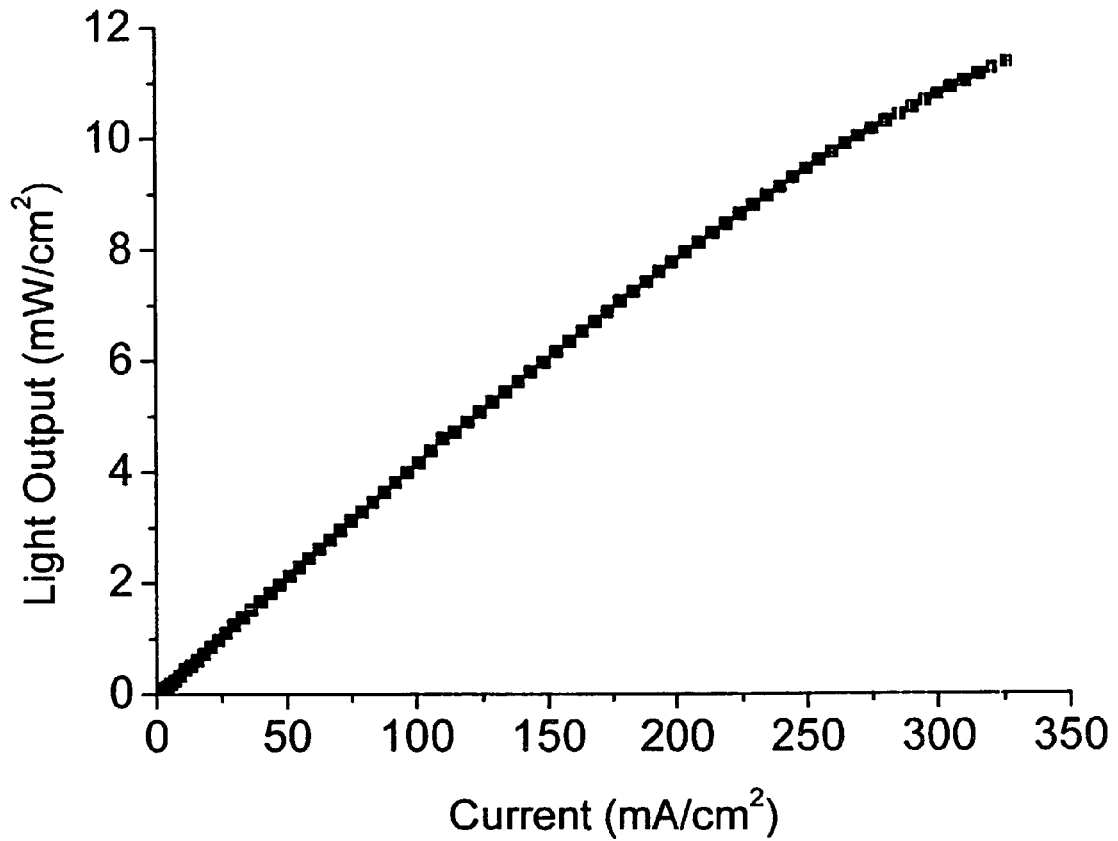
Figure 4(c): Light output-current density characteristics of device in figure 3

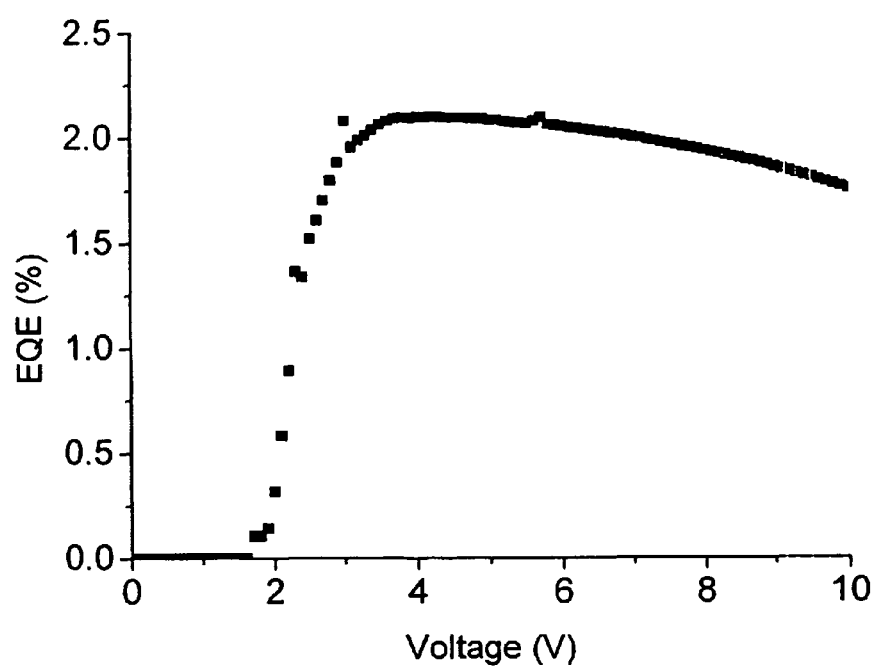
Figure 4(d): Efficiency-voltage characteristics of device in figure 3

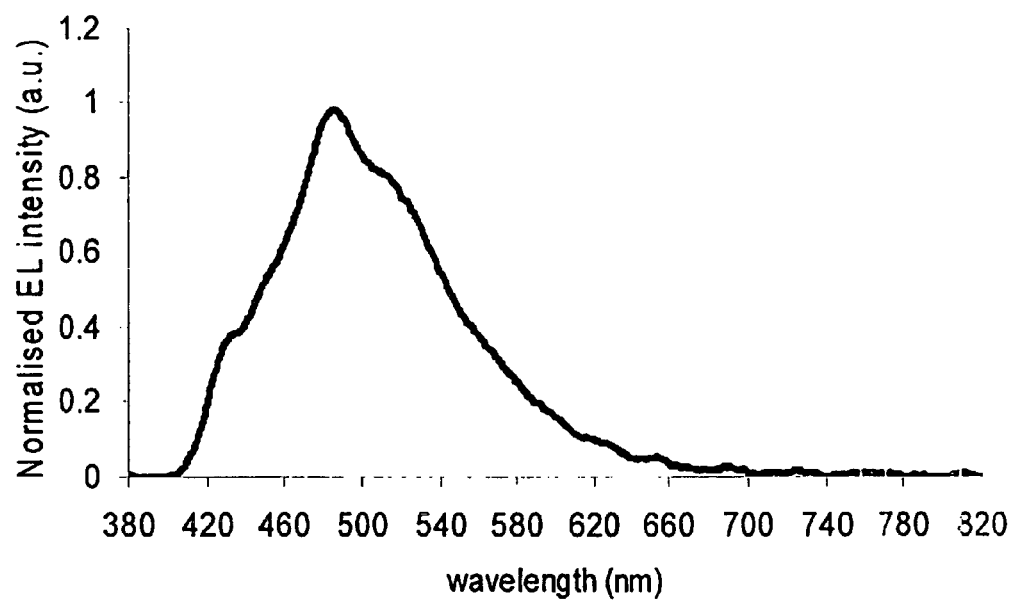
Figure 5: Spectrum of light emitted by a device using poly(dihexylfluorene) as the light-emitting layer

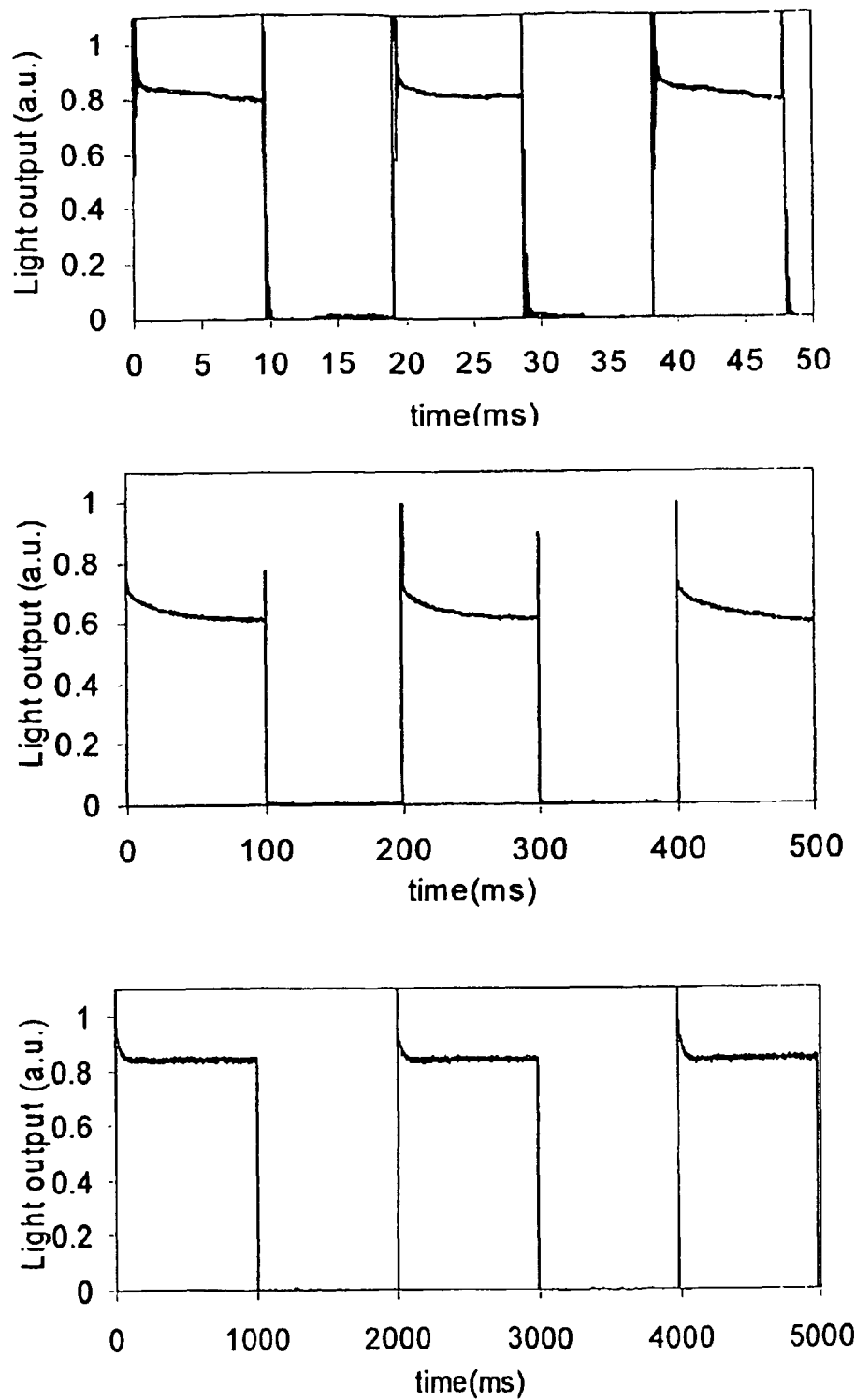
Figure 7: Light output for pulsed operation of $OC_1C_{10}$-PPV devices

THERAPEUTIC LIGHT-EMITTING DEVICE

FIELD OF THE INVENTION

The invention relates to a device for use in therapeutic and/or cosmetic treatment, particularly a treatment which involves exposure of part of the body to electromagnetic radiation. The invention also relates to such a device and a photo therapeutic agent for use therewith.

BACKGROUND TO THE INVENTION

Light can be used to treat a wide variety of diseases. When light alone is used to treat a disease, the treatment is referred to as phototherapy. Light may be used in conjunction with a pharmaceutical in which case the treatment is called photodynamic therapy (PDT). These therapies can be used to treat a variety of skin and internal diseases. In PDT, a light-sensitive therapeutic agent known as a photopharmaceutical is supplied externally or internally to an area of the body which is to be treated. That area is then exposed to light of a suitable frequency and intensity to activate the photopharmaceutical. A variety of photopharmaceutical agents are currently available. For example there are topical agents such as 5-aminolevulinic acid hydrochloride (Crawford Pharmaceuticals), methylaminolevulinic acid (Metfix®, Photocure). There are also injectable drugs used primarily for internal malignancies, including Photofin® (from Axcan) and Foscan® (from Biolitech Ltd). Often, the drug is applied in a non-active form that is metabolised to a light-sensitive photopharmaceutical.

In photodynamic therapy, the primary technique for supplying light to the photopharmaceutical is to project light of a suitable wavelength from standalone light sources such as lasers or filtered arc lamps. These sources are cumbersome and expensive, and are therefore only suitable for use in hospitals. This leads to inconvenience for the patient, and high cost for the treatment. High light irradiances are needed in order to treat an acceptable number of patients per day (for the treatment to be cost effective) and to avoid unduly inconveniencing the patient.

WO 98/46130 (Chen and Wiscombe) discloses arrays of LEDs for use in photodynamic therapy. The small LED sources taught therein result in uneven light incident on the patient. Fabrication of arrays is complicated because of the large number of connections required. The devices shown therein are designed for hospital treatment.

GB 2360461 (Whitehirst) discloses a flexible garment which uses a conventional photodynamic therapy light source to produce light which is then transmitted through optical fibres. As such light sources are heavy, the device is not ambulatory and is limited to hospital use.

U.S. Pat. No. 5,698,866 (Doiron et al) discloses a light source using over-driven inorganic LEDs. The resulting light output is not even. A heat-sinking mechanism is required, and the device is suitable only for hospital treatment.

WO 93/21842 (Bower et al) disclose light sources using inorganic LEDs. Although transportable, the device is not suitable for ambulatory use by a patient at home and clinical treatment is envisaged.

A further problem with existing approaches is that it can be difficult to achieve uniform illumination with such sources, especially on curved body parts.

SUMMARY OF THE INVENTION

According to a first aspect of the present invention there is provided an ambulatory device for use in a therapeutic and/or cosmetic treatment, the device comprising an organic light-emitting semiconductor which, in use, covers an area to be treated and emits electromagnetic radiation to cause said treatment of the area.

Preferably, the device is for use in the treatment of a human or animal patient by photodynamic therapy.

Preferably, the organic semiconductor is operable to emit light in the wavelength range of 300-900 nm.

Organic semiconductors are lightweight, and can readily be powered by portable low voltage power supplies, such as batteries, forming a totally self-contained portable unit. Indeed, the photo-therapeutic device may to advantage include a power supply for operating the organic light-emitting semiconductor. The device is sufficiently portable to enable ambulatory treatment i.e. treatment in which the patient can move around freely. It can be subsequently removed in the patient's own time, so that treatment could take place at home or at work. This gives greater convenience and lower cost (from avoiding either an out-patient or in-patient stay in hospital). It also means that lower light levels can be used since exposure can occur for a longer period of time. This overcomes a problem of pain induced in some patients by the high irradiances from conventional sources used in hospitals. In addition lower irradiance is more effective in PDT due to reduction of the extent of photobleaching of the photopharmaceutical.

Preferably, the light emitting semiconductor provides an extensive light emitting area. In contrast to point sources (such as inorganic light emitting diodes) a more even light output is thereby produced. The light emitting semiconductor preferably has an extent of at least 1 $cm^2$ and preferably is in the range 3 $cm^2$ (for small lesions) through to 100 $cm^2$ although semiconductors as large as 400 $cm^2$ might be used for a head. Preferably also, the light emitting surface of the semiconductor is continuous. The light emitting surface may conveniently be square, e.g. 1 cm×1 cm, 2 cm×2 cm, 5 cm×5 cm, 10 cm×10 cm, or circular.

The device may be planar, or may be curved in advance or in situ to conform to the surface of the area to be exposed to light from the organic light-emitting semiconductor.

Preferably, the device is flexible so as to be capable of being formed into any of a number of possible different configurations in advance or extemporaneously to the shape of the body part to which it is to be applied. The device may be disposable, i.e. used to deliver one treatment and then thrown away.

The device may be used as a stent, for example a tube of 1.25-2.25 cm radius of say 10-12 cm length for use inside the oesophagus.

Preferably, the device includes a transparent or translucent substrate layer of preferably even thickness which additionally functions as a support layer for the organic light-emitting semiconductor. The support layer can also act as a barrier layer and be selected to prevent oxygen and/or moisture from penetrating the organic light-emitting semiconductor and is preferably glass. A glass/plastic laminate structure may also be used and there may be a further barrier layer overlying the organic light-emitting semiconductor.

The device conveniently includes an adhesive surface for attaching the device to a patient.

For planar devices, the preferred substrate is glass. However, as organic semiconductors can be flexible, flexible devices can be made using a combination of flexible components (including the substrate). Indium tin oxide (ITO) coated polyester is a suitable substrate though its inferior barrier properties mean that devices using this substrate require storage (or packaging) in an inert atmosphere. Another substrate that can be used is a laminate of alternate layers of plastic and a suitable glass. Such laminates or indeed a single glass layer if sufficiently thin, can display a suitable elastic quality to be useable in a flexible device.

Preferably, the organic light-emitting semiconductor is an organic light-emitting diode. Preferably the light-emitting diode comprises a layer of the conducting polymer PEDOT/PSS which assists with hole injection into the light-emitting layer, reducing the operating voltage of the device. The light-emitting diode, may comprise an organic light-emitting layer of $OC_1C_{10}$-PPV (see FIG. 2) which can readily be made into films by spin-coating and gives orange-red light emission. The light-emitting semiconductor may be based on small organic molecules, light-emitting polymers, light-emitting dendrimers or other organic light-emitting semiconductor materials.

A multilayer organic semiconductor structure is only one option and a single organic semiconductor layer can fulfill the required functions, namely that electrons and holes are injected at opposite contacts, transported in the layer where capture of opposite charges then forms an excited state which can then emit light. A single semiconducting layer device can be used with a further layer of the conducting polymer PEDOT on an indium tin oxide layer.

The devices may be provided with a photochemical and/or a photopharmaceutical preparation present. This may be in the form of a gel, ointment or cream. Alternatively, or as well, the device may be provided with a thin film impregnated with the photopharmaceutical. Typically, the photopharmaceutical preparation is provided as a layer in contact with the light source. Provided that the photopharmaceutical preparation is transparent or sufficiently translucent for the frequency of stimulating light, the resulting device can be readily applied without a separate step of applying the photopharmaceutical to a patient. Creams which would scatter the light may nevertheless be used if they are absorbed before the light source is switched on. A photopharmaceutical layer may be covered by a peelable release medium, such as a silicone-backed sheet. The photopharmaceutical preparation may comprise an inactive compound which is metabolised in vivo to an active compound. Delivery of the photopharmaceutical can be assisted by iontophoresis.

The output of light from the organic light-emitting semiconductor may be pulsed and an electronic control circuit or microprocessor may be provided to control this pulsing and/or other aspects of device function such as duration of exposure(s) of the area to be treated and the intensity of emitted light. Pulsed devices may be provided with a preparation of a photochemical and/or a photopharmaceutical substance which is photobleachable or which is metabolised in vivo to a photobleachable chemical species.

The output of the semiconductor may take the form of a train of pulses, preferably in which the duration of the pulses is substantially the same as the interval between successive pulses. The period of the pulse train may, for example, be in the range of 20 ms to 2000 s, depending on the photobleaching characteristics of said substance.

According to a second aspect of the present invention there is provided an ambulatory device for use in therapeutic treatment (preferably by photodynamic therapy), the device comprising a light-emitting layer, wherein the device including said layer is flexible so that, when applied to a curved part of a body, the light-emitting layer conforms to the shape of the surface of the area to be treated.

Preferably, the device includes attachment means comprising an adhesive surface to enable the device to be attached to a patient.

Further preferred features correspond to the first aspect above.

According to a third aspect of the present invention there is provided an ambulatory device according to the first or second aspect above and a photo-therapeutic chemical, preferably a photopharmaceutical agent for use in photodynamic therapy, for use with the device.

The pulsing of the light used to activate a phototherapeutic chemical can also be advantageous in rigid devices or, devices having types of light source, for example a laser, other than organic semi conductors.

Thus, according to a further aspect of the invention, there is provided an ambulatory device for use in photodynamic therapy, the device comprising an electromagnetic radiation source, attachment means for attaching the electromagnetic radiation source to a patient and control means for activating and deactivating the source to cause the latter to emit a train of light pulses for activating a photodynamic chemical, whilst reducing the effects of photo bleaching on the chemical.

Preferably, the ambulatory device is provided with a photochemical and/or a photopharmaceutical preparation present. Preferred features of the preparation and its delivery are as above. In particular, the photochemical and/or photopharmaceutical may be photobleachable or may be metabolised in vivo to a photobleachable chemical species.

The means for activating and deactivating the source may control other aspects of device function such as duration of exposure(s) of the area to be treated and the intensity of emitted light.

The control means may to advantage be operable to cover the source to emit a pulse train having any one or more of the preferred features of the pulse train produced by a device in accordance with the first aspect of the invention.

BRIEF DESCRIPTION OF THE DRAWINGS

An embodiment of the present invention will now be described, by way of example only, with reference to the following figures in which:

FIG. 2 is the chemical structure of the polymer $OC_1C_{10}$-PPV used in the device; and FIG. 3 is a graph of the spectrum of light emitted by a therapeutic device including $OC_1C_{10}$-PPV as the light emitting layer;

FIGS. 4(a) through 4(d) are graphs of the current voltage characteristics, the light output-voltage characteristics; the light output-current density characteristics and the external quantum efficiency-voltage characteristics respectively of the device of FIG. 3;

FIG. 5 is a graph of the spectrum of light emitted by a device in which the light-emitting layer is poly(dihexyfluorene);

FIGS. 7(a) through (c) illustrate the light output from $OC_1C_{10}$-PPV devices operated with pulses of period (a) 20 ms, (b) 200 ms, (c) 2000 ms.

DETAILED DESCRIPTION

Figure 1:
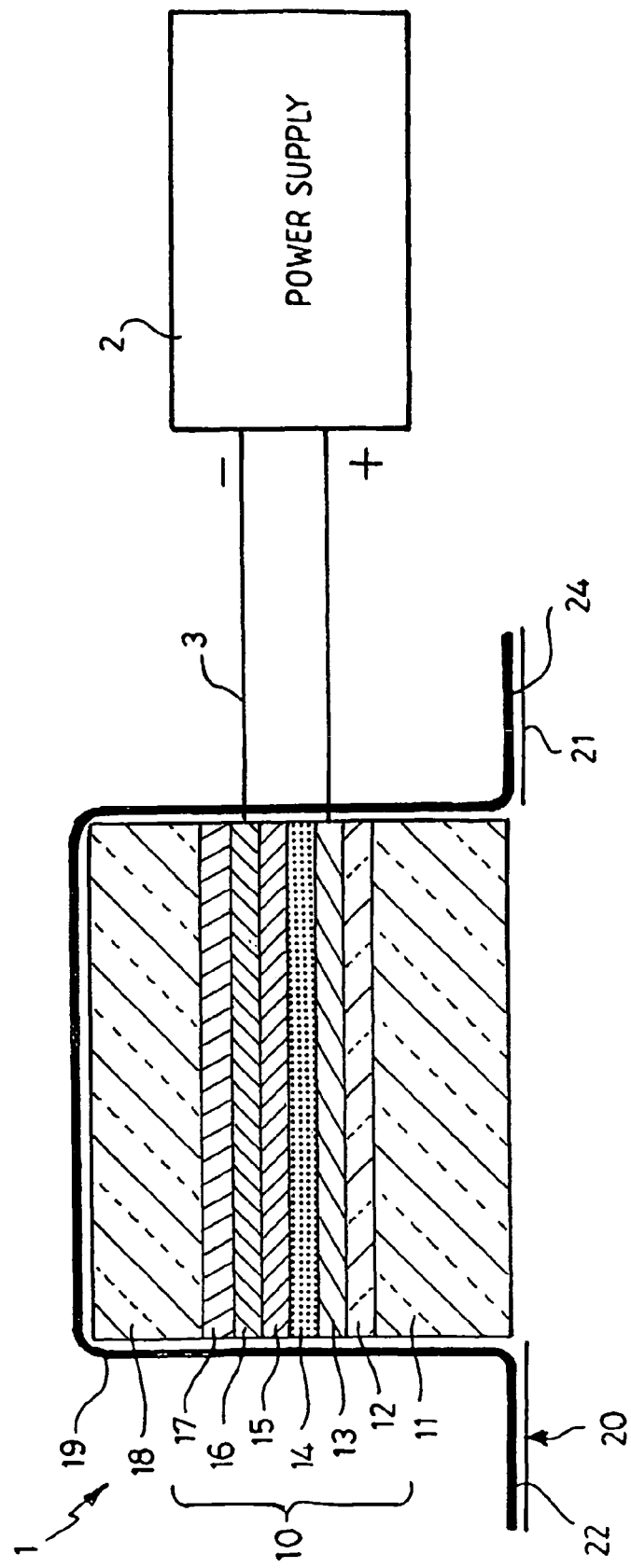
FIG. 1 is a schematic cross-section through a therapeutic device according to the present invention.

A photo-therapeutic device shown generally as 1 is connected to by way of leads 3 to a battery power supply 2. The photo-therapeutic device comprises a light-generating element shown generally as 10 which is powered by the power supply 2.

The light generating element 10 comprises an organic light-emitting diode using a layer of the polymer $OC_1C_{10}$-PPV as the light-emitting layer 14 in between suitable contacts. The hole injecting contact consists of an indium tin oxide coated glass substrate (11 and 12) coated with a layer 13 of the conducting polymer poly(3,4-ethylenedioxyhiophene) doped with polystyrenesulphonate (PEDOT/PSS). The electron injecting contact is a layer of calcium 15 which is chosen because of its low work function and is capped with aluminium 16. Light emission occurs when a current is passed between the contacts.

The lower electrode layer 12 and the glass substrate 11 are transparent. Glass is a suitable material as it also has the properties of being transparent and both oxygen and waterproof. An upper support layer 18, also formed from glass, acts as a barrier to water and oxygen, provides additional mechanical support and is attached to the upper electrode layer 16 and is sealed by means of an epoxy layer 17. Adhesive tape 19 extends over the light-generating element 10 and beyond the element 10 to provide adhesive surfaces 22 and 24 for attaching the device to a patient. Prior to attachment, these surfaces are protected by removable plastics films 20 and 21.

FIG. 2 illustrates the chemical structure of $OC_1C_{10}$-PPV. The main features are a conjugated backbone enabling charge transport, and giving an energy gap in the visible region of the spectrum. The alkoxy substituents confer solubility, and thin films of the polymer can readily be prepared by spin-coating.

Light is passed to the patient's skin from the light-generating element 10 through the transparent substrate 11. In a first example, the transparent lower support layer 11 and upper support layer 18 are planar and rigid, giving mechanical strength. Batteries are a suitable power supply with control electronics incorporating controls for time of exposure, including the possibility of a delayed start to allow a photopharmaceutical to be metabolised into its photoactive form. Controls for brightness and pulsing may be included.

An example of a method of making the device will now be described. The indium tin oxide coated glass substrate 11 and 12 (Merck $20\Omega/\square$) was cleaned by ultrasound in acetone followed by propan-2-ol (10 minutes of each). After drying, and an optional step of exposure to an oxygen plasma, a layer of the conducting polymer PEDOT/PSS (Bayer Baytron VP A14083) was spin-coated from aqueous solution at a spin speed of 2200 rpm for 1 minute. The film was baked at 80° C. for 3 minutes. The light-emitting polymer $OC_1C_{10}$-PPV (see FIG. 2) was then deposited by spin-coating a solution of 5 mg/ml of the polymer in chlorobenzene at a speed of 1750 rpm. The resulting film was in the region of 100 nm thick. This and subsequent fabrication steps were carried out in the inert atmosphere of a nitrogen glove box. The structure was loaded into an evaporator (Edwards 306) to allow the deposition of the top contact. A thin layer of calcium (25 nm) was evaporated thermally, followed by a thicker layer (140 nm) of aluminium. The pressure during the evaporations was $1.5\text{-}5\times 10^4$ mbar, and the two metals were deposited without breaking the vacuum. The above layers were then encapsulated by a glass layer 18 attached with epoxy resin 7. Adhesive tape 19 was applied and covered by a plastics films 20 and 21.

In order to test the device it was connected to a power supply (Keithley 2400 source measure unit). The light-emitting area was 1 $cm^2$. When a voltage (in the range 3-10 V) was applied, orange light emission through the substrate was observed. The device generated an irradiance in the range 0-10 $mW/cm^2$ which is considerably lower than those generated by conventional sources, such as lasers and filtered lamps, as these typically generate irradiances in the region 75-150 $mW/cm^2$. Alternatively the device could be driven by applying a current, and the intensity of the light was approximately proportional to the current supplied. The spectrum of the light emitted is shown in FIG. 3. The device is applied to skin by removing the plastic films 20 and 21 and allowing the adhesive tape to stick to the skin.

The current-voltage, light output-voltage, light output-current density characteristics and the external quantum efficiency (EQE)-voltage characteristics are shown in the form of graphs in FIGS. 4(*a*) through 4(*d*).

A similar device was made using poly (dihexylfluorene) as the light-emitting layers, giving emission in the blue-green region of the spectrum, as shown in the graph of FIG. 5.

Figure 6:
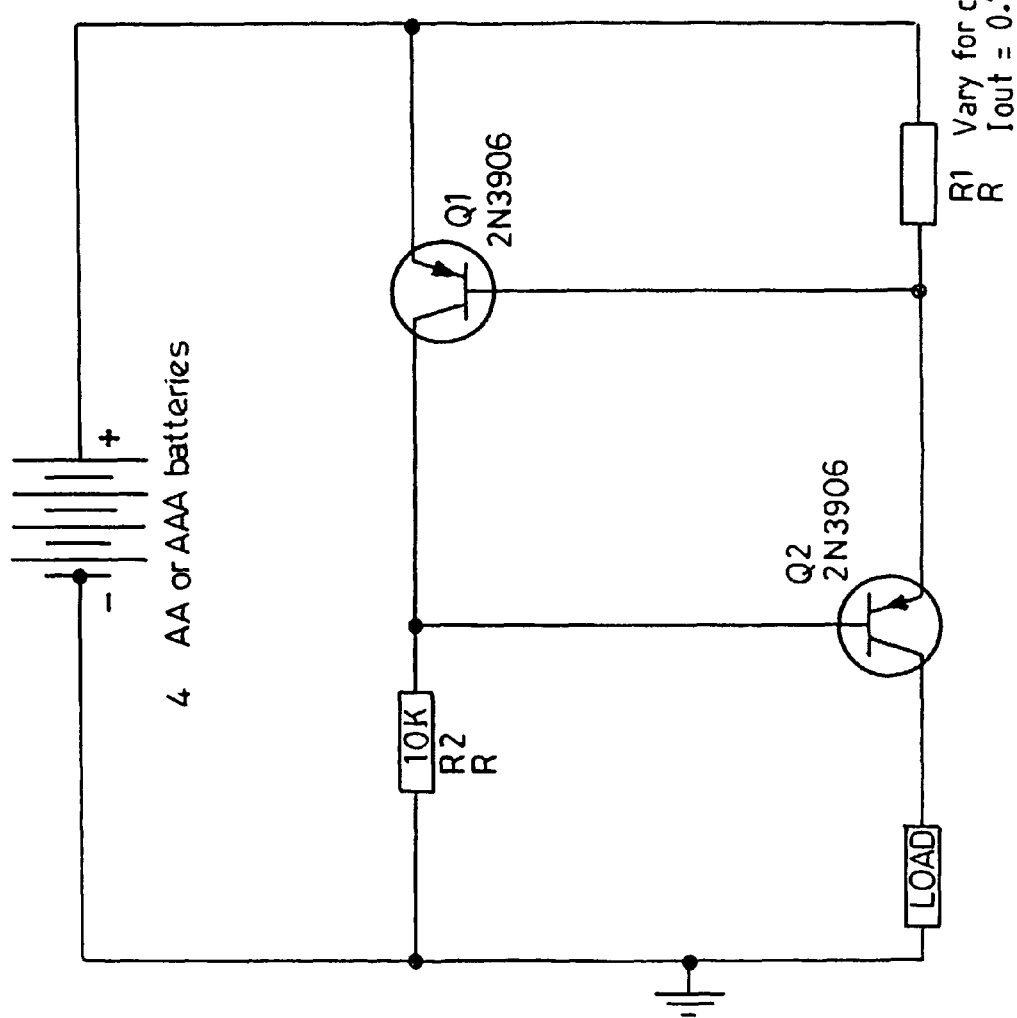
FIG. 6 is a circuit-diagram of a 108 gram power source for use with the invention.

The 1 cm×1 cm device weighed 1.26 g and was used with a 108 g battery power source, providing a light-weight ambulatory device. The power source consists of 4 conventional AA batteries and the simple current regulating circuit of FIG. 6. The 108 g power source also provides suitable power output for a 2 cm×2 cm device. A 200 g battery pack can power a 5 cm×5 cm device.

The device could be used for skin and internal disorders. A range of pre-malignant, malignant and inflammatory diseases would be the target. Examples of pre-malignant skin disease are Bowen's disease, solar keratosis, arsenical keratosis, Paget's disease and radiodermatitis. Malignant diseases include all types of basal cell carcinomas, squamous cell carcinomas, secondary metastases, cutaneous T-cell lymphomas. Inflammatory skin diseases include all types of dermatitis and psoriasis.

Further diseases that are potential targets are a range of pre-malignant, malignant and non-cutaneous disorders such as primary and metastatic tumours, as well as inflammatory disorders, eg connective tissue disease, all types of arthritis, inflammatory bowel disease.

Photopharmaceuticals can undergo reversible light-induced change, especially at high irradiances, which reduces the effectiveness of subsequent treatment—an effect referred to as photobleaching.

As reversible photobleaching of the photopharmaceutical is known to result in reduced penetration of light into the target tissue, a modified version of this device has a facility automatically to switch on and off the irradiation so delivering the desired dose, limiting photobleaching and enabling fresh uptake/metabolism of the photopharmaceutical within remaining viable target cells. This would have the clear benefit of increasing therapeutic effectiveness. The pulse trains constituting the light-output of such pulsed devices (periods 20, 200, 2000 ms) are shown in FIG. 7. Pulsed operation with a period of 20 s, 200 s and 2000 s was also demonstrated and longer periods can be envisaged. Pulse shape and duration can readily be optimised for a particular application by experiment and calculation. In the examples shown, each period is constituted be a pulse and an interval between it and the next pulse, the interval being the same as the duration of the pulse.

The light-emitting device would be used either on its own as a simple light source applied to the skin or via an internal appliance such as a nasogastric tube, chest drain or stent. For skin lesion management, the device would be used either alone or in combination with the photopharmaceutical in a translucent base such as a gel or ointment applied as a single dressing. Creams which scatter light may be used if they are sufficiently absorbed into the skin. A range of photopharmaceutical agents are currently available and it is expected that new agents of greater specificity and phototoxic effect will emerge. Examples of topical agents presently used include 5-aminolevulinic acid hydrochloride (Crawford Pharmaceuticals), methylaminolevulinc acid (Metfix, Photocure).

Injectable drugs used in the main for internal malignancies, are two in number, Photofrin (Axcan) and Foscan (Biolitech).

A second example of the invention consists of a flexible device. Here the substrate consists of a polyester film in place of glass layer 11. Layers 12 to 16 are as for the first example. Epoxy layer 17 is very thin, and layer 18 is polyester. The inferior barrier properties of the plastic layers 11 and 18 mean that this device must be stored (or packaged) in an inert atmosphere such as dry nitrogen, but can be operated in air.

In this example, the element 10 is able to flex to fit the shape of a part of the patient's body, such as the arm. In this example, the transparent support layer and upper support layer are made from a thin flexible glass, a plastic/glass laminate or indium tin (ITO) coated polyester. The latter would be stored in an inert atmosphere until it is used.

Further alterations and amendments can be made by one skilled in the art within the scope of the invention herein disclosed. For example, the invention could be used, with a photopharmaceutical, in a cosmetic treatment, and/or have veterinary, as well as medical, applications.

The invention claimed is:

1. An ambulatory device in the form of a conformal patch for use in a therapeutic and/or cosmetic treatment, the device comprising a single extensive organic light-emitting semiconductor which, in use, is ambulatory, covers an area to be treated and emits electromagnetic radiation to cause said treatment of the area, the light-emitting semiconductor having an extent of at least 1 $cm^2$ and providing even illumination and even intensity on the treatment area.

2. An ambulatory device according to claim 1 in which the light-emitting semiconductor has a surface area in the range 1 $cm^2$ to 400 $cm^2$.

3. An ambulatory device according to claim 2 in which the light-emitting semiconductor has a surface area in the range 3 $cm^2$ to 100 $cm^2$.

4. An ambulatory device according to claim 1 for use in the treatment of a human or animal patient by photodynamic therapy.

5. An ambulatory device according to claim 1 which is adapted to conform to the surface of the area to be exposed to light from the organic light-emitting semiconductor.

6. An ambulatory device according to claim 1 which is flexible so as to be capable of being formed into any of a number of possible different configurations in advance or extemporaneously to the shape of the body part to which it is to be applied.

7. An ambulatory device according to claim 1 which includes a transparent or translucent substrate layer.

8. An ambulatory device according to claim 1 which includes an adhesive surface for attaching the device to a patient.

9. An ambulatory device according to claim 1 wherein the organic light-emitting semiconductor is an organic light-emitting diode.

10. An ambulatory device according to claim 1 including control apparatus for causing the semiconductor to emit a train of pulses, and wherein light output from the organic light-emitting semiconductor is pulsed.

11. An ambulatory device according to claim 10 wherein the light output is pulsed with a period of at least 2 s, at least 20 s, at least 200 s or at least 2000 s.

12. An ambulatory device as claimed in claim 1 further comprising a photopharmaceutical preparation which comprises an inactive compound which is metabolised in vivo to an active compound.

* * * * *